(12) United States Patent
Bullard

(10) Patent No.: US 8,388,524 B2
(45) Date of Patent: Mar. 5, 2013

(54) MEDICAL INSTRUMENTS HAVING VIDEO CAPABIILITY

(76) Inventor: J. Roger Bullard, Augusta, GA (US)

( * ) Notice: Subject to any disclaimer, the term of this patent is extended or adjusted under 35 U.S.C. 154(b) by 69 days.

(21) Appl. No.: 13/029,353

(22) Filed: Feb. 17, 2011

(65) Prior Publication Data

US 2012/0215069 A1 Aug. 23, 2012

(51) Int. Cl.
*A61B 1/267* (2006.01)
(52) U.S. Cl. ...................................................... 600/188
(58) Field of Classification Search .................. 600/104, 600/109, 112, 185, 188, 194, 197, 199
See application file for complete search history.

(56) References Cited

U.S. PATENT DOCUMENTS

| | | | |
|---|---|---|---|
| 4,086,919 A | 5/1978 | Bullard | |
| 4,742,819 A | 5/1988 | George | |
| 4,807,594 A | 2/1989 | Chatenever | |
| 4,844,071 A | 7/1989 | Chen et al. | |
| 4,905,669 A | 3/1990 | Bullard et al. | |
| 5,003,963 A | 4/1991 | Bullard et al. | |
| 5,682,199 A * | 10/1997 | Lankford | 348/72 |

* cited by examiner

*Primary Examiner* — Eduardo C Robert
*Assistant Examiner* — David Comstock
(74) *Attorney, Agent, or Firm* — Barnwell Whaley Patterson & Helms, LLC

(57) ABSTRACT

An improved medical instrument having a rigid blade, a handle, a power source, and an easily removable video imaging device such as a video monitor is provided. The distal end comprises a series of channels extending along the blade in which one houses a fiber optic illuminating bundle for transmitting light into an area beyond said distal end of the blade, another channel carries an image bundle for transmitting visual images from said area to a position adjacent said proximal end of said blade and a third channel houses an intubation tube installation device or other instrument. The images are carried through the channel and the handle to the video imaging device. A quick release adaptor is connected through a hollow tube containing the image bundle to the laryngoscope handle at the end opposite the blade. The video imaging device is attached to the adaptor and may be easily release or detached therefrom.

11 Claims, 6 Drawing Sheets

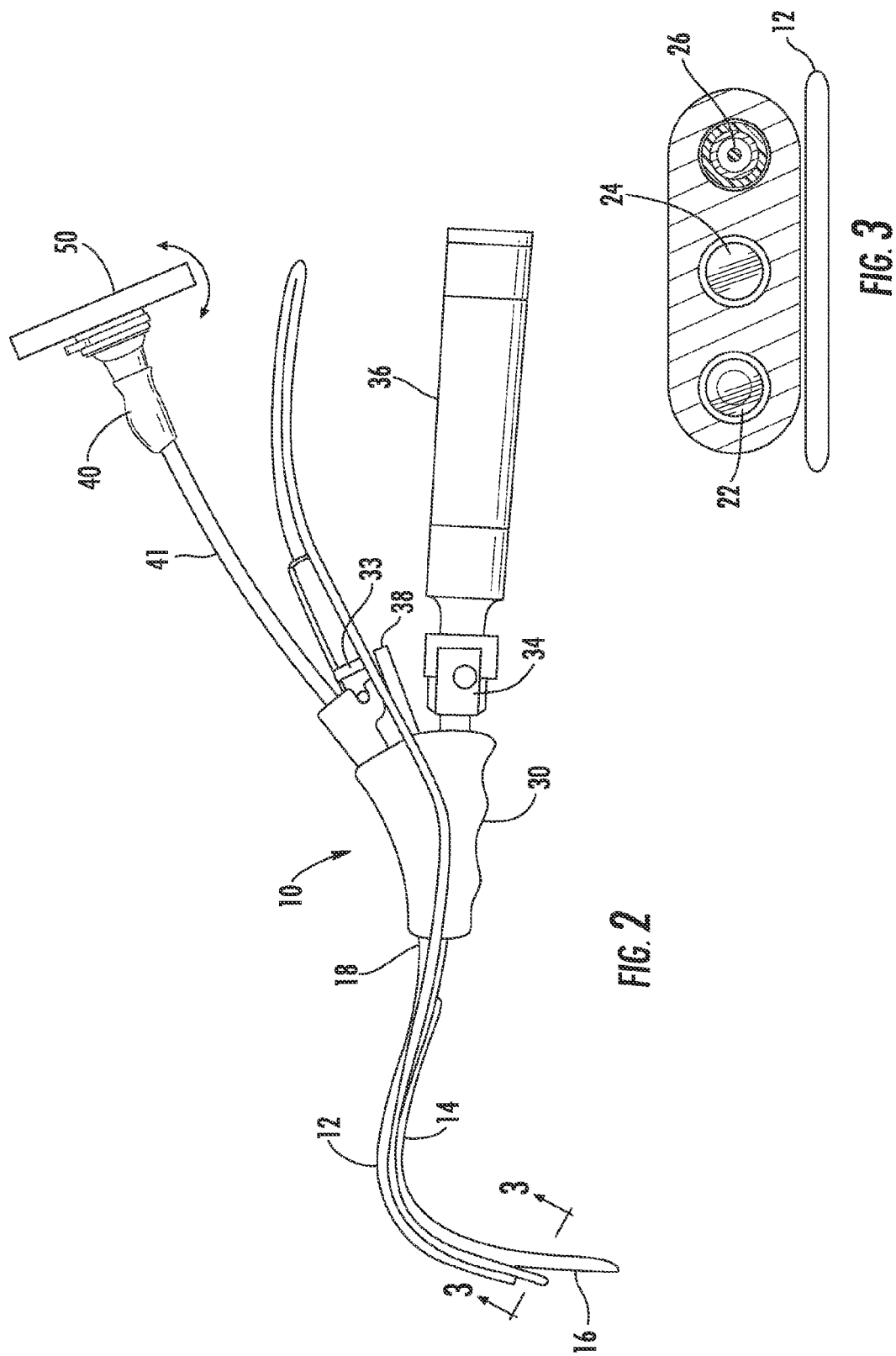

MEDICAL INSTRUMENTS HAVING VIDEO CAPABIILITY

BACKGROUND OF THE INVENTION

1. Field of the Invention

The present invention relates to improved medical instruments for visualizing interior portion of the human anatomy. More particularly, the present invention relates to an improved laryngoscope having an adapter for connecting a laryngoscope to a readily detachable video imaging device, such as a video monitor.

2. Description of Related Art

The field of laryngoscopy includes medical diagnostic and therapeutic disciplines which utilize laryngoscopes to view the laryngeal area of the throat with minimal intrusion. Laryngoscopes are anatomically shaped rigid fiber optic instruments designed to aid intubation, i.e., to facilitate endotracheal intubation of a patient during surgery to provide a positive air passageway for the administration of anesthesia and/or for the mechanical ventilation of the lungs of a patient.

By way of background, the epiglottis normally over lies the glottis opening into the larynx to prevent the passage of food into the trachea during eating; therefore, in endotracheal intubation, it is necessary to displace the epiglottis from the glottal opening to permit the air tube to be inserted into the trachea. An illustration of this area of the human anatomy is illustrated in U.S. Pat. No. 5,003,963, which is incorporated herein by reference.

Various laryngoscope constructions are known. The more widely used laryngoscopes comprise an elongate, rigid metal blade which is supportably attached to a handle and is inserted through the mouth of the patient into the pharyngeal area to displace the tongue and epiglottis and permit direct visualization of the glottis through the mouth opening. These laryngoscopes have a curved blade and are provided with a light source which is directed along the blade to illuminate the area beyond the distal end of the blade, and thus, function as an indirect fiber optic laryngoscope providing rapid, direct visualization of the larynx.

For many years the standard method for performing intubation of the trachea during surgery with rigid laryngoscope blades is to place the patient in supine position, tilt the head backwards as far as possible, and distend the lower jaw to widely open the mouth into the throat passageway to displace the tongue and epiglottis and expose the opening at the upper part of the larynx, between the vocal cords, known as the glottis.

One example of such laryngoscope has means for indirect illumination and visualization of the pharyngeal areas of the body and various iterations of laryngoscopes are found in U.S. Pat. Nos. 4,086,919; 4,905,669; 5,003,963; and 5,643,221. These patents disclose laryngoscopes for endotracheal intubation which include a rigid blade and flexible or articulatable tubular probes having internal fiber optics for lighting and viewing the larynx.

A drawback of laryngoscopes typically found in the prior art is the requirement that the practitioner view through an eyepiece located on the scope itself. This requires the physician to place an eye against the eyepiece while holding the instrument in place. Recent innovations to overcome this problem have focused on the idea of a video laryngoscope. Laryngoscopes having permanent or separate video imaging devices are known. In one type of video laryngoscope the images are carried to a viewing screen separate for the laryngoscope. One disadvantage of using medical instruments having a separate imaging screen is that they require extensive external accessories, such as video systems, monitors and wires and thus are usually quite expensive. Also the image is not convenient to the operator as the operator's head must turn to see the image. Another type of laryngoscope has the video monitor permanently attached to the body of the laryngoscope. Thus, the video attachment may not be easily removal for sterilization.

Accordingly, it would be desirable to have an improved laryngoscope having an adapter to couple a laryngoscope to a corresponding video monitor for use in video laryngoscopy. The adapter should be capable of quickly and easily releasing the monitor from the laryngoscope so that the laryngoscope may be sterilized for later use. In addition, the quick release adapter should enable the user to easily change monitor. Further, the adapter and monitor should not add much additional weight to the laryngoscope.

SUMMARY OF THE INVENTION

It is therefore the general object of the present invention to provide a video monitoring system made to fit all types of ocular-equipped medical scopes, laryngoscopes, bronchoscopes, nasopharyngoscopes, cystocopes, gastroscopes and arthroscopes.

Another object of the present invention is to provide a medical instrument that has a quick release attachment for releasing a video imaging device so that the instrument may be sterilized.

Another object of the present invention is to provide a laryngoscope that has a video monitor that is small size, e.g., approximately the size of a deck of playing cards.

Yet another object of the present invention is provide as laryngoscope having video capabilities such that more than one operator can view the interior portion of the human anatomy during the procedure.

There is provided a laryngoscope having a rigid blade, a handle, a power source, and an easily removable video imaging device, such as a video monitor. The distal end comprises a series of channels extending through the blade in which one channel houses a fiber optic illuminating bundle for transmitting light into an area beyond the distal end of the blade, another channel carries an image bundle for transmitting visual images from that area to a position adjacent the proximal end of the blade and a third channel work channel that houses an intubation tube or other medical instrument. The images are carried through the channel and the handle to the video imaging device. Illumination for the laryngoscope can be provided by either a standard laryngoscope battery holder or a fiber optic light source.

A quick release adaptor is connected through a hollow tube containing the image bund to the laryngoscope handle at the end opposite the blade. A video imaging device is attached to the adaptor and may be easily released or detached therefrom.

There are several advantages to using a video laryngoscope. It provides a clearer view of the area which can make difficult intubations easier and speed up regular intubations. One of the advantages of the medical instruments of the present invention is that because the video monitor is easily removable from the body of the instrument, the instrument is easily sterilized. Another advantage is that there are no external accessories needed, such as video systems, monitors, or wires and thus the medical instrument is readily portable and thus the medical instruments of the present invention are less expensive than those with separate imaging devices.

Other objects, features and advantages of the present invention will become apparent from the following detailed description of the invention taken in conjunction with the accompanying drawings.

BRIEF DESCRIPTION OF THE DRAWINGS

Having described the invention in general terms, reference will now be made to the accompanying drawings, which are not necessarily drawn to scale, and wherein:

FIG. 2 is a side view of the laryngoscope shown in FIG. 1 illustrating the major parts of the laryngoscope;

FIG. 3 is a cross-sectional view of the blade of the laryngoscope in FIG. 2 taken along line 3-3 illustrating an image channel, a fiber optic illuminating bundle channel and a working channel;

DESCRIPTION OF THE PREFERRED EMBODIMENT(S)

The present invention now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be through and complete and will fully convey the scope of the invention to those skilled in the art. Like numbers refer to the elements throughout.

Figure 1:
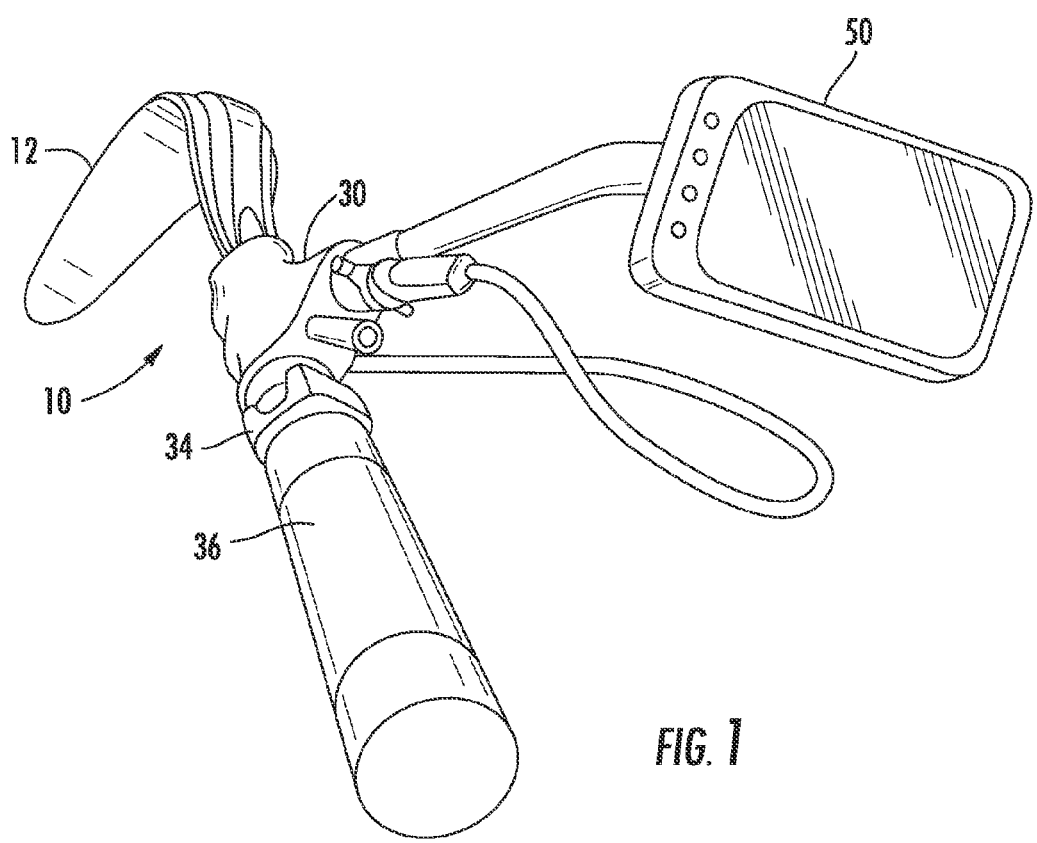
FIG. 1 is a perspective view of the laryngoscope of the present invention illustrating the adapter and quick release video monitor.

Generally speaking, FIG. 1 shows an overview of the laryngoscope 10 of the present invention illustrating a laryngoscope scope, having a rigid elongated blade 12, a handle 30, a power source 34 and an image viewer 50. It should be understood that although the invention if described in relation to a laryngoscope that it is equally adaptable to other medical instruments such as bronchoscopes, nasopharyngoscopes, cystocopes, gastroscopes and arthroscopes.

Referring now to FIG. 2 there is shown video laryngoscope 10 of the present invention intended for use for inserting an intubation or endotracheal tube into the trachea of a patient. More specifically, laryngoscope 10 comprises rigid elongated blade 12, a handle 30, a power source 36 exemplified by a battery, an image viewer 50, exemplified by a video monitor, and a stylet port 33. The elongated blade 12 has an anatomically curved configuration having an anterior, or inner, curved surface 14 and a width greater than its thickness in the transverse direction. The elongated blade is constructed of a suitable high strength material, such a metal or plastic. The elongated blade 12 has a distal end 16 intended for leading insertion into the patient's mouth and a proximal end 18 connected to the handle 30.

In FIG. 3 there is shown a cross-sectional view of the distal end 16 of the blade 12. The distal end 16 comprises a series of channels extending through the blade to the handle, in which channel 22 is provided to house a fiber optic illuminating bundle, a channel 24 carrying an image bundle, and a working channel 26. Although there are three channels shown in relatively linear arrangement in this embodiment, any number of channels may be used and the channels may be arranged in any suitable type of configuration.

The illumination bundle in channel 22 is connected to a suitable light source (not shown) and transmits light to the distal end 16 of the elongated blade 12 into an area beyond the distal end of the blade, e.g., the laryngeal area of the throat. The image channel 24 is provided to house a bundle of image transmitting fibers for transmitting visual images from the laryngeal area. This bundle is connected to a suitable image viewing device 50, such as a video monitor and transmits images of the areas proximate the distal end 16 of elongated blade 12 to the image viewing device 50 for observation. The working channel 26 is provided for housing an intubation tube installation device or other instrument. The working channel 26 communicates from the distal end 16 of blade 12 through the handle 30 to the stylet port 33. The proximal end 18 of elongated blade 12 is connected to handle 30, which serves as a means for the practitioner to hold and guide the elongated blade and to view the transmitted images of the laryngeal area.

Illumination for the laryngoscope 10 can be provided by either a standard laryngoscope battery holder 32 or a fiber optic light source. FIG. 2 shows a typical standard laryngoscope battery holder 32 attached to the laryngoscope handle 30 through connecting member 34. The battery holder 32 preferably lies along an extension of the longitudinal axis of the blade, rather than at an angle thereto. By so locating the holder 32 the area above the patient is free from obstruction by the laryngoscope and is thus more easily accessible to be viewed through the video imaging device 50 and also more available for other surgical procedures. The battery holder 32 retains a power source such as dry cell batteries (not shown). The batteries communicate with a light source (not shown) which provides light to the fiber-optic illumination bundle in channel 22. It should be understood that any suitable light source configuration can be used. The battery holder 32 of this embodiment is also disconnectable from the handle 30 for such occasions as cleaning or storage.

Standard introducing stylets are provided and connect directly to the laryngoscope through stylet port 33. The stylets allow simultaneous introduction of the bundles and endotracheal tube through the channels in the blade, ensuring optimal control. A standard luer connector 38 provides suctioning of secretions, administration of oxygen, or application of local anesthetics.

Due to the thin anterior-posterior dimension and the anatomically curved shape of the blade, it is easily passed between the teeth and through the oral and pharyngeal passageways to a point adjacent the epiglottis. As the pharyngeal and laryngeal areas are indirectly viewed through the video imaging device 50, the upwardly turn tip of the blade 12 is inserted into the velecula. By merely raising laryngoscope handle 30 a short distance in the vertical direction, the tongue is lifted and retained on the blade and the epiglottis raised to expose the glottis and permit visualization of the glottis and larynx through the camera.

Figure 4:
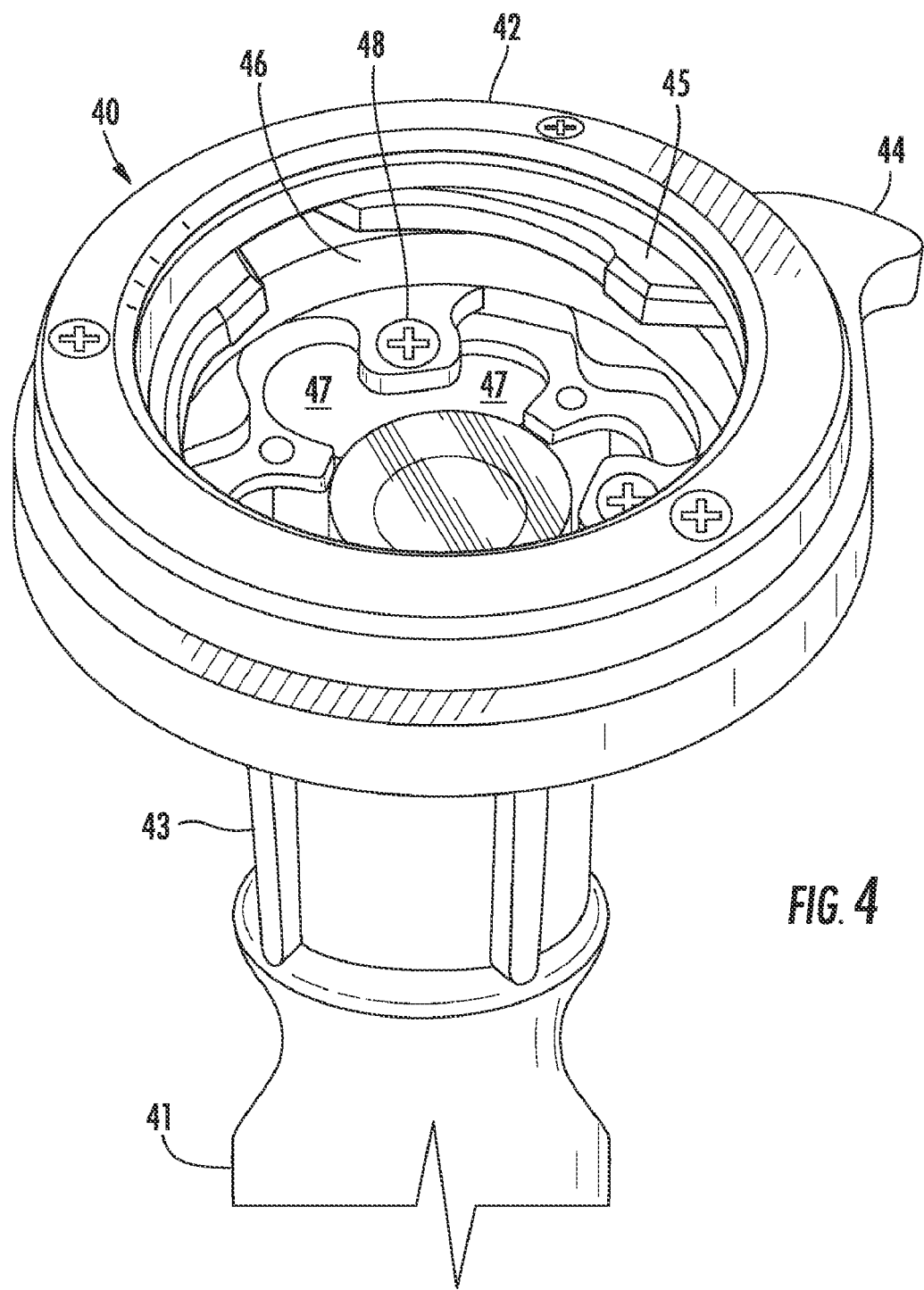
FIG. 4 is a pictorial view of the quick release adaptor of the present invention used to connect the body of the laryngoscope to the video monitor.
Figure 5A:
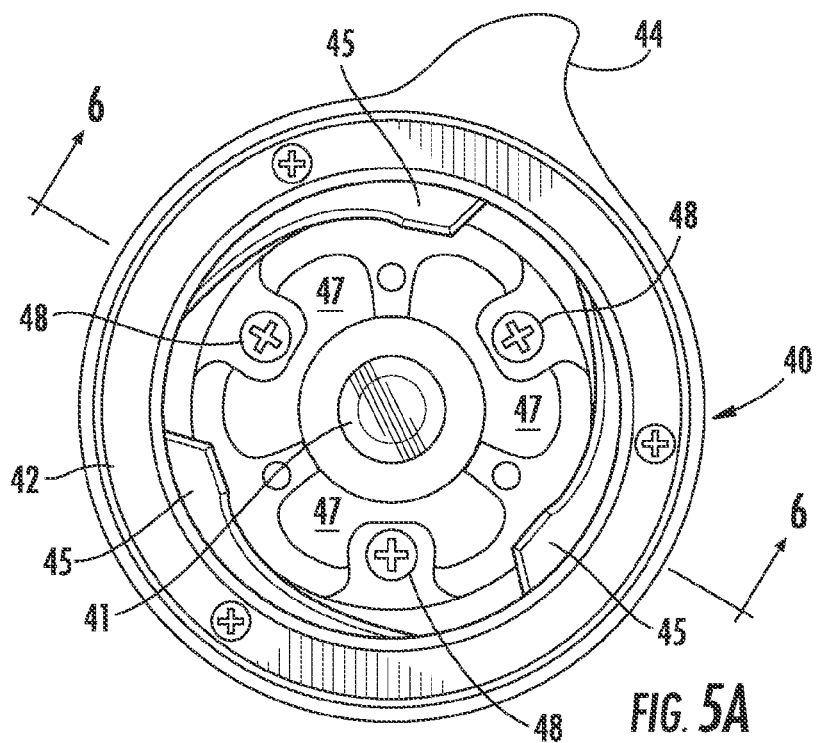
FIG. 5A position is an end view of the quick release adapter shown in FIG. 4 showing the monitor connection in a closed position.
Figure 5B:
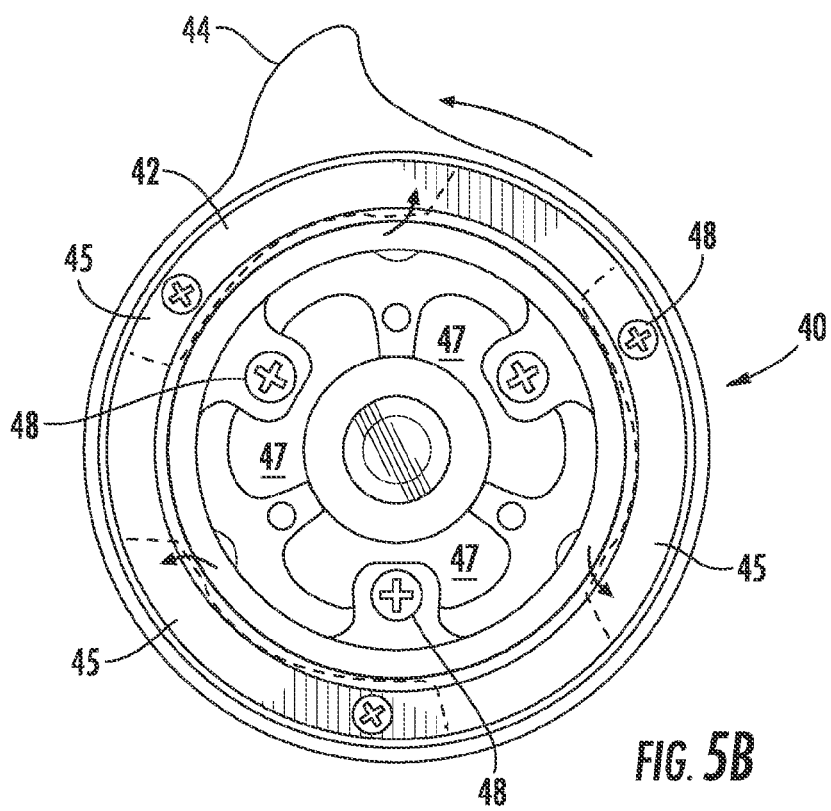
FIG. 5B is an end view of the adapter shown in FIG. 4 showing the quick release monitor connection in an open position.
Figure 6:
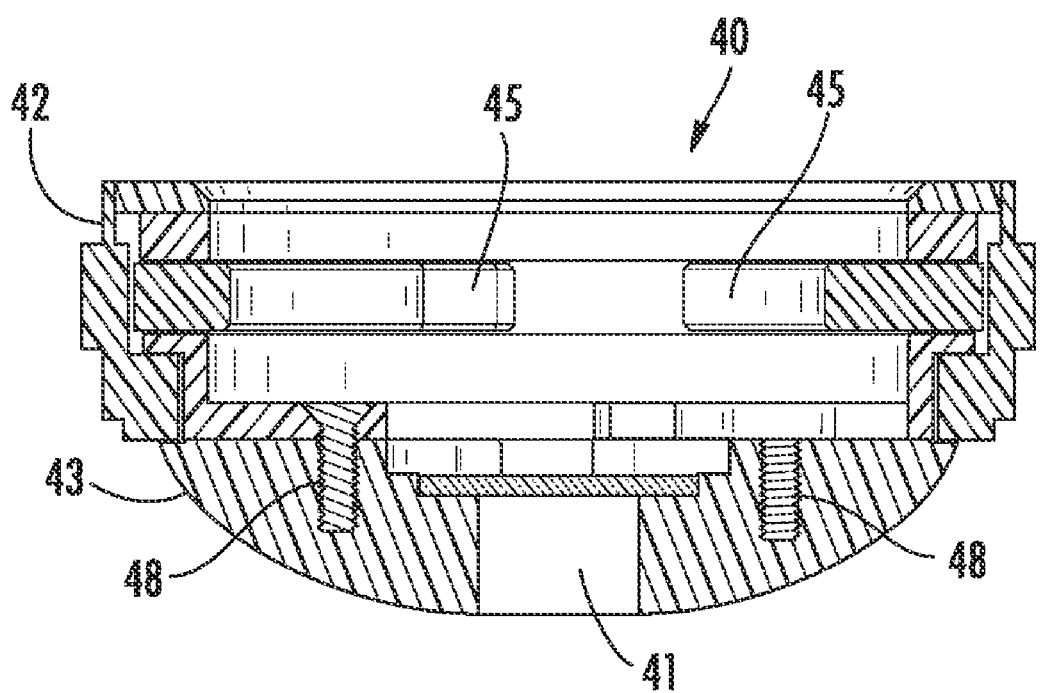
FIG. 6 is a partial cross-sectional view of the adapter taken along line 6-6 in FIG. 4.

A conventional laryngoscope includes an eyepiece for viewing images of the laryngeal area. The eyepiece typically includes a flared flange for facilitating viewing of the laryngoscope by the operator. However, the present invention comprises a means for optically coupling a medical instrument, such as a laryngoscope, to a video imaging device. For example, as shown in FIGS. 4-6, adapter 40 is provided to couple the laryngoscope handle 30 through which the image bundle passes to a video imaging device, such as video monitor 50. The video adaptor can be used on any medical instrument that has an ocular equipped eye-piece, similar to those shown in found in U.S. Pat. Nos. 4,086,919 and 5,643,221, for example.

Thus, as shown in FIG. 2, a quick release adaptor 40 attaches to the handle 30 at the opposite side from the blade 12 through a hollow tubular channel 41 through which the image bundle and the illumination bundle pass. As shown in FIG. 2 the length of the hollow tubular channel 41 is long enough for the adapter 40 to be in a position for the video imaging device 50 to be easily used, when attached. In one embodiment of this invention the tubular channel 41 is made of a flexible material so that the video imaging device 50 may be adjusted by the operator for easier viewing.

The adapter 40, as shown in FIG. 4 has a body 42. The adapter body 42 is connected to the tubular channel 41 at connection 43 by screws 48. The interior of the adapter body 42 is open to accommodate locking arms 45 controlled by quick release lever 44. As shown in the end view of FIG. 5A of the adapter shows the locking arms 45 is a closed position; whereas in FIG. 5B the quick release lever 44 is moved counterclockwise placing the locking arms 45 in an open position. To attach the video imaging device 50 to the adapter, the locking rim 53 of the device is placed in the hollow portion of the adapter body 42 and the lever 44 is moved clockwise to a closed position locking the video imaging device firmly in position as shown in FIG. 6. The adapter body 42 also includes air vents 47. Other locking means such as a bayonet type locking system may be used.

Figure 7:
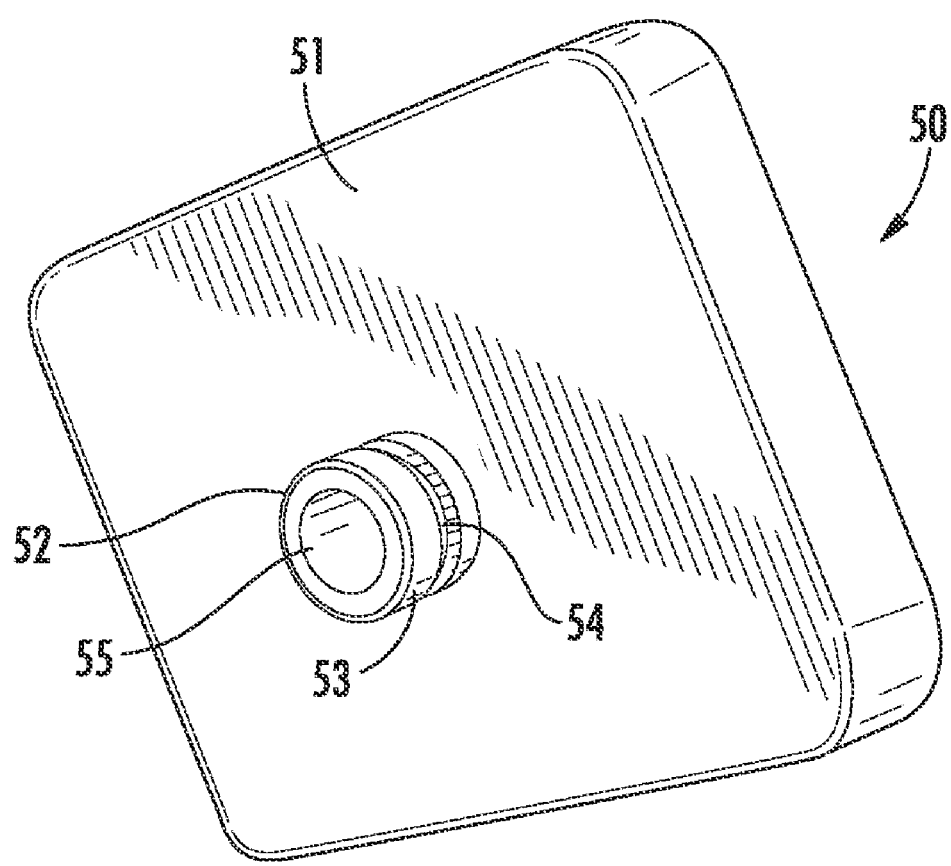
FIG. 7 is a rear view of a connection for the video monitor.

The heart of the video laryngoscope lies in the imaging device 50 which fits into adaptor 40 and may be easily release or detached therefrom. A preferred imaging device 50 is a video monitor approximately the size of a deck of playing cards. Suitable monitors are well known to those skilled in the art. The video imaging device sends the light source through the laryngoscope as well as returns the image to the video system. The video imaging device 50 is also where the practitioner controls the multiple aspects of image control. As shown in FIG. 7 the rear 51 of video imaging device 50 has a connecting post 52 and an opening 55 through which the images are passed. The connecting post 52 includes recess 54 and locking rim 53. When the video imaging device 50 is connected to the adapter 40 the adapter locking arm 45 fits into recess 54 and is held in place by locking rim 53.

In view of the description above it is easy to see that the medical instruments of this invention have a low cost because, among other reasons, they do not require a separate video screen and do not require external wiring. A further advantage is the video attachment has an internal battery.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A medical instrument having an adapter for coupling a video imaging device thereto comprising:
    a rigid elongated blade having a distal end and a proximal end and having a width greater than its thickness;
    said proximal end of said elongated blade being connected to a handle,
    an illuminating channel extending along the length of said blade for transmitting light into an area beyond said distal end of said blade, and
    an image channel extending along the length of said blade for transmitting visual images from said area to a position adjacent said proximal end of said blade,
    a hollow tube having one end attached to the end of said handle opposite said elongated blade and the other end attached to an adapter body, said image channel passing through said flexible hollow tube,
    said adapter body having an interior that is open to accommodate a quick release locking mechanism, and
    a video imaging device engaging means capable of being connected to said quick release locking mechanism.

2. The medical instrument according to claim 1 wherein said medical instrument is a laryngoscope.

3. The medical instrument according to claim 1 further comprising a power source, for transmitting said light through said illuminating channel into an area beyond said distal end of said blade.

4. The medical instrument according to claim 1 further comprising a detachable video imaging device.

5. The medical instrument according to claim 4 wherein said detachable video imaging device is a video monitor.

6. The medical instrument according to claim 4 wherein the rear of said video imaging device further comprises a means whereby said video imaging device is attached to said quick release locking mechanism.

7. The medical instrument according to claim 6 wherein said locking means is a bayonet-type locking means.

8. The medical instrument according to claim 1 wherein said hollow tube is flexible.

9. A laryngoscope comprising:
    a rigid elongated blade having a width greater than its thickness and having a distal end and a proximal end connected to a handle, said elongated blade containing an image bundle comprising;
    an illuminating channel extending along the length of said blade for transmitting light into an area beyond said distal end of said blade,
    an image channel extending along the length of said blade for transmitting visual images from said area to a position adjacent said proximal end of said blade, and
    a working channel extending the length of said blade;
    a flexible hollow tube having one end attached to the end of said handle opposite said elongated blade and the other end attached to an adapter body, said image channel passing through said flexible hollow tube,
    an adapter body connected to said flexible hollow tube, the interior of said adapter body being open to accommodate a quick release locking mechanism, and a quick release locking mechanism within said adapter body; and
    a video imaging device capable of being connected to a quick release locking mechanism.

10. The laryngoscope according to claim 9 wherein the interior of said adapter body has locking arms connected to a quick release mechanism for engaging said video imaging device.

11. The laryngoscope according to claim 10 wherein the rear of said video imaging device further comprises a means whereby said video imaging device is attached to said quick release locking mechanism.

* * * * *